(12) United States Patent
Mosier et al.

(10) Patent No.: US 7,968,504 B2
(45) Date of Patent: Jun. 28, 2011

(54) TRANSESTERIFICATION COMPOSITION OF FATTY ACID ESTERS, AND USES THEREOF

(75) Inventors: Benjamin Mosier, Houston, TX (US); Bryan J. Duffy, Lubbock, TX (US)

(73) Assignee: MJ Research and Development, LP, Houston, TX (US)

( * ) Notice: Subject to any disclaimer, the term of this patent is extended or adjusted under 35 U.S.C. 154(b) by 612 days.

(21) Appl. No.: 11/821,689

(22) Filed: Jun. 25, 2007

(65) Prior Publication Data

US 2008/0020956 A1 Jan. 24, 2008

Related U.S. Application Data

(63) Continuation of application No. 09/921,238, filed on Aug. 2, 2001, now Pat. No. 7,252,779.

(60) Provisional application No. 60/222,477, filed on Aug. 2, 2000.

(51) Int. Cl.
*C10M 159/12* (2006.01)
*C10M 141/10* (2006.01)

(52) U.S. Cl. ........ 508/419; 508/421; 508/486; 508/487; 508/501

(58) Field of Classification Search .................. 508/419, 508/421, 486, 487, 501; 44/300
See application file for complete search history.

(56) References Cited

U.S. PATENT DOCUMENTS

| | | | |
|---|---|---|---|
| 1,822,977 A | 9/1931 | Munz | |
| 3,524,751 A | 8/1970 | Smith et al. | |
| 3,755,385 A * | 8/1973 | Hutchins | 554/167 |
| 4,101,432 A | 7/1978 | Okorodudu | |
| 4,152,915 A | 5/1979 | Bussi et al. | |
| 4,626,444 A | 12/1986 | Takahashi et al. | |
| 4,704,165 A | 11/1987 | Nakamura et al. | |
| 4,963,280 A | 10/1990 | Wilkins et al. | |
| 5,468,405 A * | 11/1995 | Klein et al. | 508/486 |
| 5,681,915 A | 10/1997 | Lechner et al. | |
| 5,908,818 A | 6/1999 | Egawa et al. | |
| 5,916,854 A | 6/1999 | Inaya et al. | |
| RE36,293 E | 9/1999 | Mizui et al. | |
| 5,976,399 A | 11/1999 | Schnur | |
| 5,997,761 A | 12/1999 | Kaneko | |
| 6,001,273 A | 12/1999 | Minor et al. | |
| 6,002,030 A | 12/1999 | Valbert | |
| 6,013,194 A | 1/2000 | Minor | |
| 6,013,609 A | 1/2000 | Katafuchi | |
| 6,018,063 A | 1/2000 | Isbell et al. | |
| 6,019,909 A | 2/2000 | Ide et al. | |
| 6,026,649 A | 2/2000 | Adachi | |
| 6,030,934 A | 2/2000 | Owens et al. | |
| 6,090,989 A | 7/2000 | Trewella et al. | |

FOREIGN PATENT DOCUMENTS

| | | |
|---|---|---|
| EP | 0967197 | 12/1999 |
| FR | 2374290 | 7/1978 |
| GB | 457548 | 8/1935 |
| GB | 563481 | 8/1944 |
| GB | 591421 | 8/1947 |
| WO | WO 9015127 | 12/1990 |
| WO | WO 9222627 | 12/1992 |
| WO | WO 9222631 | 12/1992 |

OTHER PUBLICATIONS

Haller et al., "Comptes Rendus Hebdomadaires des Seances de L'Academie des Sciences" 1907 pp. 462-466 Gauthier-Villars, Paris, FR.
M.J. Diamond et al., "Preparation of Phosphorus Esters of Long Chain Hydroxy Fatty Acids" J. of Am. Oil Chemists' Society v. 41 1964 pp. 9-13.

* cited by examiner

*Primary Examiner* — Ellen M McAvoy
*Assistant Examiner* — Latosha Hines
(74) *Attorney, Agent, or Firm* — Bracewell & Giuliani LLP

(57) ABSTRACT

This invention is a composition that includes a transesterified fatty acid ester resulting from the reaction of a fatty acid ester, in the presence of an acid, with a hydroxyl-containing compound. The fatty acid esters of the invention are selected from those with a carbon number of eight to twenty. The hydroxyl-containing compound is an alcohol having a carbon number between one and eighteen. The resulting composition is useful as a lubricant, as a heat transfer agent, as a rheological modifier and as a corrosion/moisture inhibitor, among other uses.

31 Claims, No Drawings

TRANSESTERIFICATION COMPOSITION OF FATTY ACID ESTERS, AND USES THEREOF

This application is a continuation application which claims priority to and the benefit of U.S. patent application Ser. No. 09/921,238, filed on Aug. 2, 2001 now U.S. Pat. No. 7,252,779, which claims priority to and the benefit of U.S. Provisional Patent Application Ser. No. 60/222,477, filed Aug. 2, 2000 by Benjamin Mosier and Bryan J. Duffy, entitled Lubricant and Refrigerant Oil System.

BACKGROUND OF THE INVENTION

1. Field of the Invention

This invention relates to transesterified fatty acid esters and the reaction products of a fatty acid ester, in the presence of an acid, with a hydroxyl-containing compound. This composition is useful as a lubricant and as a heat transfer agent, among other uses.

2. Description of the Prior Art

There are a vast number of lubricants and lubricant additives found in the market place today. Many of these lubricants have undesirable compounds for long-term use in a mechanical system. Others exhibit only a limited degree of miscibility in an oil-based system. Common to most of these lubricants is a rather low upper-limit of pressure resistance before the lubricant fails.

U.S. Pat. No. 5,916,854 issued to Inaya et al discloses a biodegradable lubricant base oil. The Inaya biodegradable lubricating base oil is obtained by carrying out an addition reaction of an alkylene oxide and a transesterification in a mixture of fats and oils, a polyhydric alcohol or an aliphatic carboxylic acid and an alkylene oxide. Further, a biodegradable lubricating oil composition containing the biodegradable lubricating base oil and the use thereof are also described. The Inaya patent describes one particular derivative material obtained from fats and oils that shows desired biodegradability and desired stability to thermal oxidation.

It is an object of the current invention to provide a composition and a method of lubricating wherein the lubricant additive is readily miscible in an oil-based system. It is an object of the current invention to provide a composition and a method of lubricating where lubrication is achieved even at low miscibility between the composition and an oil-based system. It is an object of the current invention to provide a lubricant or lubricant additive that is useful at extremely low and extremely high temperature regions. It is an object of the current invention to provide a lubricant or lubricant additive that is useful at extremely high pressures. It is an object of the invention to provide a lubricant or lubricant additive that is not corrosive. It is an object of the invention to provide an additive or working fluid that acts as a corrosion inhibitor.

Fluorinated hydrocarbons have long been used as a refrigerant. In recent years, concern that the fluorinated hydrocarbons are damaging the ozone layer has created a demand for refrigerants that do not deplete the ozone. U.S. Pat. No. 5,976,399 issued to Schnur discloses a blended polyol ester lubricant for refrigerant heat transfer fluids including an ester having neopentylglycol and a source of 2-ethylhexanoic acid as its reactive components. Alternately, an ester having pentaerythritol and a source of 2-ethylhexanoic acid is used. This specific ester was shown to be useful as a lubricant and for a refrigerant heat transfer fluid. Mutual miscibility between the refrigerant and lubricant of the refrigerant working fluid is important to avoid separation of the two.

The closest known methods of performing related functions in the improvement in the energy efficiency of heat pump systems are those including the halogenated a-olefins, the most common of which utilizes the chlorine molecule. (Refer to U.S. Pat. No. 4,963,280) The disadvantage of the chlorine compound is the possibility of a chlorine free radical becoming exposed to moisture resulting in the formation of hydrochloric acid and subsequent corrosion. Additionally, these halogenated compounds are extremely hygroscopic exposing the system to potential moisture contamination.

One of the difficulties experienced using with prior art has been the failure to control the nature of the sludge or deposit and the location of its deposition. Sludges plug lubricating paths and prevent the delivery of an adequate supply of lubricant. Generally, the prior art refers to sludges and deposits as having a high coefficient of friction, low thermal conductivity, ability to readily polymerizes and carbonizes, as being oxidatively unstable and lacking strong adhesive and cohesive properties due to polarity.

It is an object of this invention to provide a method for lubricating surfaces and reducing friction and wear.

It is an object of this invention to allow for the simplification of the mechanical design of machinery and equipment by providing a lubricating method which requires a very simple lubricating means as the reduction in the coefficient of friction.

An object of this invention is to provide a lubricating method wherein there is an automatic supply or replenishment of lubricant to surfaces in friction which acts as a non-insulating and thermally conductive layer while providing heat transfer under low and high loads.

A particular object of this invention is to provide a refrigeration oil lubricant that is compatible with naphthenes, paraffins, alkyl benzenes, mineral oil, polyol esters, polyalphaolefins, polyalkylene glycols, polybutenes and polyvinyl ethers.

It is an object of the current invention to create a heat transfer fluid that does not deplete the ozone. It is an object to develop a composition that acts as a lubricant in a heat exchange fluid. It is the object to develop a composition that acts as an additive but which can also serve as a complete lubricant or working fluid in some cases.

Various objects and mechanical systems are subject to corrosion from working or environmental conditions. Mechanical systems are equipment with moving parts or static physical pieces. It is an object of the current invention to present a composition effective to inhibit corrosion. Similarly, various objects and mechanical systems are susceptible to moisture. It is a further object of the current invention to present a composition effective in inhibiting moisture.

There are numerous fluids that have utility where it is desirable to change the rheological properties of such fluids. Examples of such working fluids include drilling fluids and cutting fluids. Frequently, viscosity is a key property to influence. It is an object of the current invention to present a composition effective to modify the rheological properties of the fluid.

It is an object of this invention to provide a lubricant that is stable at low temperatures, i.e., below 0° C., and elevated temperatures, i.e., above 350° C.

It is an object of this invention to provide a lubricant that possesses boundary lubrication properties.

It is an object of this invention to provide a composition that is highly surface active, hence good detergency.

It is an object of this invention to provide a lubricant that has a low coefficient of friction.

It is an object of this invention to provide a composition which displaces other lubricants that are less polar and substantive than the transesterified fatty acid esters.

BRIEF SUMMARY OF THE INVENTION

The current invention, which addresses one or more of the above objects, includes a novel composition. We have found that the aforementioned objectives can be achieved by a method having the steps of supplying a hydrocarbon medium containing reactive ingredients which deposit a tenacious lubricating film on the surface. The composition of the invention includes a transesterified fatty acid ester. To produce the transesterified fatty acid ester, a fatty acid ester is transesterified, in the presence of an acid, through reaction with a compound containing a hydroxyl functional group. Preferably, the fatty acid ester has a carbon number between eight and twenty-two inclusive. Dimers and trimers of these fatty acids are also useful. The composition that is the reaction product of the fatty acid ester reacted with the compound containing a hydroxyl functional group in the presence of an acid contains the transesterified fatty acid ester as well as other products resulting from the reaction. The fatty acid ester can be synthetic or naturally occurring. In a preferred embodiment, the fatty acid ester is a vegetable oil. Some of the fatty acid esters encountered in vegetable oils and useful in this invention are ricinoleic acid, oleic acid, linoleic acid, stearic acid, lauric acid, myristic acid and palmitic acid.

In a preferred embodiment, the vegetable oil is castor oil. Castor oil typically contains at least about 80 percent ricinoleic acid with about 89 percent being typical. Other fatty acid esters with a carbon number of 18 are also preferred. The balance of the castor oil includes other compositions. Synthetic fatty acid esters can also be used which would be of higher purity. In one embodiment where the fatty acid ester is castor oil, the resulting composition includes ricinoleic n-propyl ester as the transesterified fatty acid ester. In another embodiment using castor oil, the reaction produces an ester of ricinoleic acid and glycerol. One embodiment using an acid which includes phosphorus reacts to produce a phosphated fatty acid ester. This phosphorus can be directly linked or form adjuvants. Further reaction products include glycerol ricinoleate and n-propyl ricinoleate.

A preferred composition results from mixing reactants in the following proportions:

25 mol %-36 mol % of fatty acid ester;
58 mol %-62 mol % of alcohol; and
0.8-10 mol % acid.

Various compounds are produced thereby including a compound having the formula:

COOH—(CH2)$x$-(CH—O(Ac))$z$-(CH2)$y$ wherein
Ac is an acid functional group
x+y gives a resultant between 10 and 20; and
z is from 1 to 2.

In a preferred embodiment, Ac is $H_2PO_3$ or $H_2SO_4$ in the above formula. The term between is intended to be inclusive throughout. This formula is a general formula showing various compound groupings. It is not intended to show specific placement of the CH group or groups having the OAc attached.

While the slate of products produced can be difficult to categorize discretely, the product of the reaction is a substance effective in providing lubrication to a mechanical system such that the transesterified fatty acid, which is produced from fatty acid esters having carbon numbers from eight to twenty-two, has an HLB between about 0.5 and 4.8 and exhibiting in excess of 1000 pounds force load to failure. In one case, the products produced up to 3000 pounds force load to failure. When the fatty acid esters have a carbon number from twelve to eighteen, the HLB is typically between about 1.5 and 2.6. Another preferred embodiment includes fatty acid esters having a carbon number from sixteen to eighteen. Likewise a preferred embodiment includes an HLB between about 2.5 and 3.1 and exhibiting in excess of 1000 pounds force load to failure. As stated above, these fatty acid esters can be dimerized or trimerized.

DETAILED DESCRIPTION OF THE INVENTION

The Composition

The composition of the current invention is the transesterified fatty acid ester produced from a fatty acid ester reacted, in the presence of an acid, with a compound containing a hydroxyl functional group. The fatty acid ester of the invention is preferably a vegetable oil. Vegetable oils are combinations of mono, di, and triglycerides with small amounts of other compounds, such as phospholipids. A refined vegetable oil is preferred for the reaction process with synthetic fatty acid esters being an alternative embodiment. Vegetable oils predominantly characterized by fatty acid esters with carbon numbers of eight to twenty-two are preferred. More particularly, fatty acid esters of carbon numbers twelve to eighteen are preferred. Yet more particularly preferred are those of carbon number sixteen to eighteen. Vegetable oils are preferred, particularly those with a higher concentration of $C_{16}$ components such as canola and palm oil. Fatty acid esters of carbon number eighteen are particularly preferred. Ricinoleic acid is a fatty acid ester with a carbon number of eighteen that is preferred. Ricinoleic acid is the common name of the triglyceride or fatty acid ester found in various vegetable oils, particularly castor oil. Corn oil is also preferred. This can also be called ricinolein or the glyceride of ricinoleic acid. Ricinoleic acid occurs in high concentrations in castor oil. One product of reaction of castor oil includes ricinoleic propanol ester. Other fatty acid esters include oleic acid, stearic acid, lauric acid, myristic acid and palmitic acid.

Examples of various fatty acid esters include caprylic, capric, lauric, lauroleic, myristic, myristoleic, palmitic, palmitoleic, stearic, oleic, linoleic, linolenic, ricinoleic, arachidic, gadoleic, arachidonic, behenic, erucic acid and the like. All of these fatty acid esters are useful in the current invention. Natural sources of these fatty acid esters include almond, apricot kernel, avocado, castor, coconut, corn, cottonseed, olive, peanut, rice bran, safflower, sesame, soybean, sunflower, walnut, palm, canola, linseed and the like. Fatty acid esters are beneficial in that they are nontoxic, a renewable resource and biodegradable.

In a preferred embodiment, the acid useful in the reaction contains either phosphorus or sulfur. Examples of such are phosphoric acid, phosphonic acid, sulfuric acid and sulfonic acid. Other acids useful in the invention include muriatic acid, nitric acid, chloro sulfonic acid, dodecylbenzene sulfonic acid, organic sulfonic acids, acetic acid, sulfosalicylic acid, gluconic acid, citric acid, formic acid, hydroxy acetic acid, hydroxy benzoic acids and the like. When the acid contains a phosphate or a sulfate functional group, transesterified fatty esters result with an adjuvant or bonded functional group of the same. One example is the resulting transesterified fatty acid ester composition including a phosphorus-containing ester functional group, such as a phosphate ester group, and a sulfur-containing ester functional group such as a sulfate ester functional group. A preferred embodiment includes the composition having a phosphorous-containing functionality and a sulfur-containing functionality. In particular embodiments, these inorganic functional groups interact to produce reaction products containing phosphorus or sulfur other than the transesterified fatty acid.

The compound containing the hydroxyl functional group is preferably an alcohol having a carbon number from C1 to C18. Examples of alcohols useful in the invention include methyl alcohol, ethyl alcohol, butyl alcohol, pentyl alcohol, hexyl alcohol, heptyl alcohol, octyl alcohol, nonyl alcohol, decyl alcohol, dodecanol, iso-propyl alcohol, n-propyl alcohol, glycerol, substituted alcohols, multiple hydroxy functional group alcohols and the like. N-propyl alcohol is particularly useful.

The fatty acid esters of the invention, after undergoing transesterification, produce various products that are useful in this invention. Products of this reaction include one or more of glycerol ester, phosphated fatty acid ester, glycerol ricinoleate or n-propyl ricinoleate. Other specific products include phosphated ricinoleic acid, diphosphated ricinoleic acid, phosphated oleic acid, diphosphated glyceryl ricinoleate and phosphated glyceryl mono-oleate. Included are those instances when the fatty acid ester is dimerized or trimerized. Compositions of ricinoleic acid, oleic acid, stearic acid or palmitic acid are particularly useful starting materials.

Another embodiment of the composition is one wherein at least a portion of the composition includes an estolide functional group. The composition can also include a miscibility-enhancement additive effective to increase miscibility with naphthenes, paraffins, alkyl benzenes, mineral oils, polyol esters, polyalphaolefins, polyalkylene glycols, polybutenes, polyvinyl ethers and substituted hydrocarbons. The preferred miscibility-enhancement additives are C10 to C18 long chain alcohols, esters, quaternary ammonium salts, alkyl benzenes and the like. An amount effective to enhance miscibility is used. It is often desirable to use an amount from at least about 0.1 percent to about 10 percent by weight of the composition. More particularly, the miscibility-enhancement additive can be from at least about 1 percent to about 5 percent by weight of the composition. Notably, the composition is a universal lubricant in that it is effective when added to a working fluid in which it is either slightly or highly miscible.

The transesterified fatty acid of the invention can be further reacted with a second compound having an acetyl, alkyl oxy, alkyl propoxy or carboxyl functional group to form a further-substituted fatty acid ester that includes an acetyl, alkyl oxy, alkyl propoxy or ester functional group. The second compound improves miscibility with naphthenes, paraffins, alkyl benzenes, mineral oils, polyol esters, polyalphaolefins, polyalkylene glycols, polybutenes, polyvinyl ethers and substituted hydrocarbons. The second compound for improved miscibility is C10 to C18 long chain alcohols, esters, quaternary ammonium salts, alkyl benzenes and the like. Further reacting the transesterified fatty acid ester with a low molecular weight carboxylic acid or anhydride also results in esters having additional acetyl groups.

Fatty Acid Ester Chemistry

Fatty acid esters combine three reactive functional groups: double bond, alcohol and carboxylic acid. This configuration leads to the useful properties of the products. For purposes of example, castor oil will be discussed as representative of fatty acid ester chemistry. Also, ricinoleic acid, the most common fatty acid ester in castor oil, provides a versatile starting material for the syntheses of a lubricant system. The hydroxyl, carboxyl and double bond functionalities are sites for a variety of chemical reactions. The attachment of highly polar inorganic groups, such as phosphoric acid, to the point of unsaturation or to the hydroxyl group, allows for increased intermolecular bonding between adjacent ester molecules, thus increasing molecular cohesion important to the formation of durable films. The phosphate and polar carboxyl group allow for the formation of an ester "head" that strongly associates with and attaches to metal surfaces.

The three functionalities are useful in that the carboxyl position allows for a wide range of esterifications. These esterifications include transesterifications as well as coesterification and further substitution of ester groups and are jointly referred to as transesterification. The hydroxyl group can be acetylated or alkoxylated or, more generally, esterified. The unsaturation (double bond) can be altered by hydrogenation or epoxidation and phosphorylation. The hydroxyl group can be removed by dehydration to increase the unsaturation of the compound. The location of the hydroxy group proximal to the double bond stabilizes the double bond to oxidation. The double bond allows for an extreme low temperature pour point. In this way, the reaction product can be distinctly designed for performance characteristics.

The unusual sites of substitution create surprising properties for the reaction products and opportunity for further reactions. In one embodiment, transesterified fatty acid esters are further reacted to create secondary- or further-substituted fatty acid esters, including tertiary substituted fatty acid esters. This reaction proceeds with a second compound having an acetyl, alkyl oxy or carboxyl functional group to form a further-substituted fatty acid ester that includes an acetyl, alkyl oxy or ester functional group.

Castor oil readily forms estolides which result from the linkage between hydroxyl and carboxyl groups the hydroxyl group in ricinoleic acid actually forming an ester with the carboxyl group. The double bond functions to decrease the minimum working temperature of the fatty acid ester derivatives (e.g., esters) by allowing the derivatives to remain liquid at temperatures well below 0° C. The n-propyl ester of castor oil structure, with its mid chain hydroxyl and ester groups and point of unsaturation, provides excellent surface wetting and adhesion characteristics that make it ideal for many uses, one of which is as a lubricant.

Uses of the Composition

Lubricant

The composition of the invention has characteristics that make the composition particularly useful as a lubricant or as an additive to a lubricant. This invention includes a process for lubrication of a lubricant-dependant system with a fluid including adding an effective amount of the transesterified fatty acid ester of the invention to the lubricant-dependant system in the fluid.

The preferred amount of the composition of the invention for use in the fluid is an effective amount, with the effective amount of the transesterified fatty acid ester typically between about 0.5 percent to 100 percent by volume of the fluid. At less than 100 percent, the composition acts as an additive. At 100 percent, the composition of the invention is the entire working fluid. More particularly, the effective amount of the transesterified fatty acid ester is from at least about 1.5 percent to about 20 percent by volume of the fluid. Preferably, the effective amount of the composition is from about 1.5 to 10 percent. For circulating refrigerant in a refrigeration system, the effective amount of the composition is from about 5 percent to 10 percent by volume. For circulating engine oil in a combustion-type engine, the effective amount is from about 5 to 20 percent by volume. Due to the heat transfer properties of the composition, the composition can be used as the entire heat transfer fluid with lubricant properties. For improving the lubricity of a drilling fluid, an effective amount can be less than 1.0 percent by weight of the drilling fluid.

There are an infinite number of systems that require lubrication. These and other systems or pieces of equipment benefitting from the use of a lubricant are referred to jointly as lubricant-dependant systems. Due to the anti-corrosive nature of the composition of the invention, this composition is compatible with all such systems. The composition is miscible in oil-based lubricants or can act as a lubricant without additional chemical components. Examples of lubricant-dependant system include mechanical devices, refrigeration systems, motor oil systems, engines, engine parts, gears, drilling operations, reciprocating combustion engines and the like.

Extensive testing has been performed on air conditioning systems with surprising results. In addition to excellent miscibility in refrigerant oil, the composition withstands extreme temperatures and pressures without seizing or galling. The composition is capable of providing lubrication at temperatures up to about 350 degrees C. and down to about 0 degrees C. Furthermore, the composition is capable of withstanding 1000 pounds of force or more without failure.

One of the primary functions of the invention is that of a lubricant. The present invention also relates to the improvement in the energy efficiency of heat pump systems including refrigeration units, heating and air-conditioning systems which pump heat from one location to another. The invention has been tested extensively for use in automobile or vehicle air-conditioning systems, including field tests. Vehicles include automobiles, trucks, boats, tractors, recreational vehicles and the like. The invention increases the efficiency of the system through its superior properties of lubrication and its ability to greatly enhance the heat exchange capabilities related to the evaporator and condenser components of the system. The composition of the invention is that of a highly polar molecule which, in addition to having superior properties of lubricity, also acts as a thermoconductive agent thereby enhancing the heat exchange factor within the system.

The function of the present invention as a lubricant is to reduce friction and wear by separating contacting surfaces. Use as a heat transfer agent includes increased removal and dissipation of heat. The composition of the invention forms high pressure fluid seals between proximal parts such as in piston seals. The lubricant also inhibits corrosion and carries away debris caused by wear.

The distinctive qualities of the present invention as it relates to the field of general lubricants are: superior properties relative to measurements of coefficient of friction as measured by the Falix test results; biodegradable in nature; nontoxic and reduced flammability as shown through flammability tests. Also, the composition of the invention has excellent viscosity properties for allowing hydrodynamic lubrication. Alternately, the composition acts to modify the rheological properties of the fluid to which it is added to significantly improve hydrodynamic lubrication. The composition exhibits good sealing of metal joints especially under high pressure conditions such as in a piston. Tests have shown a surprisingly high pressure is achievable before failure of the lubricant such that it is particularly useful in high pressure situations. The composition provides film surface adhesive strength sufficient to remain fixed on metal surfaces to prevent part asperities from making contact and causing wear. Resulting films have lower coefficient of friction. The film cohesive integrity is sufficient to resist shear thus preventing part asperities from making contact and causing wear. Furthermore, the composition exhibits characteristics of forming a water barrier/seal to prevent corrosion and oxidation of components. It is believed that the composition, when used as an additive, brings about a reaction between the composition and the metal surface. Thus, compounds are formed such as the compounds FeS, Fe($PO_4$), organic phosphates or phosphites. Phosphates impact a crystalline discontinuous film.

Sludges plug lubricating paths and prevent the delivery of an adequate supply of lubricant. The composition of the invention maintains fluidity throughout a wide range of temperatures and has flow properties beneficial to maintaining lubricant delivery. The deposit formed with the lubricant is designed to reduce the coefficient of friction between mating surfaces. The lubricant provides sufficient adhesion to maintain a film on surfaces under dynamic conditions. Additionally, the composition used as lubricants are not heat activated and tenaciously bind to surfaces without sludge formation at temperatures below zero and in excess of 300° C. The surface-active organic ingredients employed are effective at low concentration, provide excellent sealing between proximal parts, lubricate and inhibit surface corrosion. The n-propyl ester of castor oil is stable to 350° C. making it ideal for high temperature applications. This ester also remains stable at low temperatures i.e., below 0° C., and does not solidify.

The composition of the invention lowers the pour point/freezing point of paraffinic oils therein preventing wax crystallization and film formation at low temperatures. The composition of the invention modifies friction properties, reduces wear and prevents galling and seizing. The polar ester forms physical or chemical bonds with mating surfaces that provide supplemental wearing surfaces. The composition of the invention is extremely surface active and acts as a dispersant or detergent. Sludges are kept in a dispersed state. Chemical and physical forces combine to keep sludges or deposits solubilized and dispersed, and this prevents agglomeration. Polar esters do not readily form emulsions with base fluids such as paraffinic and naphthenic hydrocarbons. The composition of the invention exhibits boundary and extreme pressure lubrication properties and contributes to oil viscosity. The composition of the invention also acts as a metal deactivator and passivator. Through the formation of a protective layer, the composition of the invention prevents the catalytic oxidation of oils by the metal substrate.

Some of the unexpected results, in comparison with other formulations for lubricants or heat exchange additives, include a reduction of oxidation, prevention of sludge formation, substantially greater reduction of friction, inhibition of corrosion and modification of viscosity. The composition operates over a surprisingly broad temperature range including temperatures considerably higher than those expected with other lubricants. The composition exhibits boundary and extreme pressure properties. The composition also, surprisingly, acts as a detergent showing not only a maintenance of cleanliness but an increase in cleanliness, such as in use with compressors. The composition of the invention greatly enhances the performance when used as an additive in mineral oil, alkyl benzenes, polyol esters, alkylene glycols, olefins and the like. The composition is compatible with elastomer seals. It improves elastomeric properties of gaskets and seals. Neoprene rubber, nitrile rubber, polyester, Teflon type seals and the like benefit from the lubrication and water repellant qualities of the composition of the invention. Furthermore, the compound is not chemically reactant with the seals.

Lubricants act to reduce static and dynamic friction by forming an intermediate film layer between mating surfaces. As long as these proximal surfaces and contact areas are completely separated by a film of lubricant, the coefficient of friction is reduced, and additionally, the two surfaces will not wear; however if the surfaces approach each other to the point where their surface asperities contact, abrasion will result. The severity of this wear depends on the amount and nature of the contact.

For heavily loaded contacts, there are three predominant modes of lubrication. Under low pressure and high tolerance, the surfaces can be separated by a relatively thick, pressurized film of lubricant that develops as a result of the motion between the surfaces. This is called hydrodynamic lubrication.

When loads are high and/or the contact area is small, interaction between the deflection of the surfaces due to the high loads and hydrodynamic action of the lubricant produces an elastohydrodynamic (EHD) film. This film is thinner than a full hydrodynamic film, but can be thick enough to prevent gross contact between the peaks of the surface asperities.

The third mode of lubrication, called boundary lubrication, depends on thin surface films to lubricate the contacting surfaces. These surface films help the parts slide over each other without the severe distress of unlubricated contact; however, when the relatively thin boundary-lubrication films fail either by wearing through or melting, asperity contact and wear of the surfaces results.

In the case of rolling bearings, gears and cams, EHD film is the predominant form of fluid-film lubrication because of high loads and small contact areas. Lubricant additives and surface films can provide for boundary lubrication in the event of periodic breakdown of the EHD film. For long life and continuous service, the conditions that enhance the formation and maintenance of the EHD film must be optimized.

The composition of the invention fulfills all three functions described above in performing its lubricant functions. The rheology, such as viscoelasticity, of the system allows for excellent hydrodynamic lubrication and relates to its unusually cohesive interfacial properties. The ability of the composition of the invention to readily wet out and adhere strongly to metal surfaces, as well as its tenacious cohesive character, promotes its application in the EHD and boundary functions.

In contrast to the composition of the invention, the so-called synthetic polyol esters are generated from the reaction of polyols, such as pentaerythitol, with mono and dicarboxylic acids. Polyol Esters (POE) fail to give comparable lubrication properties when compared to the composition of the invention. Testing of a typical POE used in the refrigerant industry, Polyol Ester 150 by National Refrigeration, showed marked lower performance to the composition of the invention when tested by means of the pin and v-block lubrication test method. Additions of the composition of the invention to the POE system over a series of increased concentrations lead to parallel increases in lubricity.

Likewise, mineral oils (naphthenes and paraffins) and alkyl benzenes, give relatively poor lubrication properties when compared to the composition of the invention. As with the addition of the composition of the invention to the POE system, the increase in lubricity of the oil system runs parallel to the introduction of ever higher concentrations of the composition of the invention. In the POE, mineral oil and alkyl benzene systems, 5-10% of the composition of the invention, also called "the ester," added to the base oil was sufficient to greatly enhance lubricity.

Short chain alcohol esters are also readily soluble in polyol ester refrigeration oils and readily miscible and dispersible in the alkyl benzenes and mineral oil refrigeration oil. Freon 22 and 134a readily disperse in the ester lubricant. The n-propyl ester of castor oil is unique in having free or esterified hydroxyl groups on the fatty acid ester chain. These hydroxyl groups and ester functionalities (both inorganic and organic) increase the solubility of the polar refrigerant gases (Freons) in the lubricating oil base. The n-propyl ester of castor oil and the other transesterified fatty acids of the invention are miscible with the polyol ester lubricants and possess high solubility in the alkyl benzene and mineral oil-based lubricants. The solubility of the n-propyl ester of castor oil can readily be extended through the addition of long chain alcohols ($C_6$-$C_{12}$) and more preferably with saturated or unsaturated fatty acid esters of short chain alcohols as isopropyl myristate. Phase transfer catalysts such as quaternary ammonium salts (e.g., Tallow or cocoa dimethyl ammonium chloride, bromide or iodide) can also be used. This highly cationic quaternary ammonium salt acts as a phase transfer catalyst based on opposition of charge of the transfer material. The composition of the invention can be used in neat form as 100% of the fluid or at a range of dilutions in lubricants such as mineral oil, alkyl benzene and polyol ester.

The wear properties of the composition of the invention are surprising, yielding superb hydrodynamic, elasto-hydrodynamic and extreme pressure lubricant performance. The composition of the invention possesses viscoelastic properties as well as provides extremely low coefficients of friction. A comparison to common lubricants such as numerous non-transesterified fatty acid esters derived from plant products such as cotton seed, linseed, canola, corn, tung, coconut, soybean, castor, mineral oil, polyol esters, polyalkylene glycols (e.g., ethoxylated castor oil), alkyl benzene, chlorinated alpha olefins, WD-40, motor oils (SAE-30), Mobil 1 Trisynthetic Formula 10W-30, Exxon Superflo 10W-40 among other oils and oil additives tested by the standard pin and v-block methods were performed.

V-block and pin testing of the composition of the invention system in its pure form, i.e., not as an additive, has demonstrated it is unsurpassed as a lubricant. Torque values below 25 lb-in were obtained at loads of 1500 lbs and torque values were below 31 at 2200 lbs. Final failure of the lubricant occurred at 2300 lbs with no weld or scarring being exhibited on the pin. Additionally, the coefficient of friction exhibited by the low torque values coincided with low frictional heat as indicated by the relatively low temperature of the oil post run. Most other lubricant systems fail prior to 600 lbs. When the composition of the invention is used as an additive in low concentrations of a common lubricant, final failure of the common lubricant can be significantly increased to as much as 1000 lbs and more.

Heat Transfer Fluid

The composition of the invention has characteristics that make the composition particularly useful as a heat transfer fluid or an additive to the heat transfer fluid. This invention includes a process for increasing heat transfer in a heat transfer system capable of receiving the heat transfer fluid by adding an effective amount of the transesterified fatty acid ester to the heat transfer fluid.

The effective amount of the transesterified fatty acid ester is typically between about 0.5 percent to 100 percent by volume of the fluid. At less than 100 percent, the composition acts as an additive. At 100 percent, the composition of the invention is the entire working fluid, in this case a heat transfer fluid. More particularly, the effective amount of the transesterified fatty acid ester is from at least about 1.5 percent to about 20 percent by volume of the fluid. Preferably, the effective amount of the composition is from about 1.5 to 10 percent. More particularly, the effective amount of lubricant is at least about 2 percent by volume of the circulating refrigerant in the refrigeration system. For circulating refrigerant in a refrigeration system, a further preferred amount of the composition is from about 5 percent to 10 percent by volume. For circulating engine oil in a combustion-type engine, the effective amount is from about 5 to 20 percent by volume. Due to the heat transfer properties of the composition, the composition can be used as the entire heat transfer fluid.

In that the composition of the invention is non-corrosive, it is universally useful in heat transfer systems. It can replace or be added to halogenated fluids. Representative heat transfer systems include coolant systems, refrigeration systems, hydraulic braking systems, hydraulic transmission systems, refrigeration systems, air conditioning systems and the like. Coolant systems are for reciprocating combustion engines, hydraulic braking systems, hydraulic transmission systems or the like. Refrigeration systems include air-conditioning system for vehicles, commercial air-conditioning systems, residential air-conditioning systems or the like. These and other uses that depend upon a heat transfer or heat exchange fluid are jointly referred to as heat transfer systems.

Refrigerant Applications include:
  Reciprocating, scroll as screw type compressors
  Centrifuged chillers
  Oil size A/C and refrigeration systems
  In systems from −65F(54C) to 400F (204C)
  With systems using R-134, R-124, R-125, R-22; R-12, 502, 400
    Methane series R-10 to R-50
    Ethane series R-110 to R-170
    Propane series R-216 to R-290
    Ammonia
    Butane
    Compatible with $SO_2$ (R-76C) and $CO_2$ (R-744)

As discussed above, halogenated a-olefins are commonly used in heat pump systems, the most common of which utilizes the chlorine molecule. The disadvantage is the possibility of a chlorine free radical becoming exposed to moisture resulting in the formation of hydrochloric acid and subsequent corrosion. Additionally, these halogenated compounds are extremely hygroscopic exposing the system to potential moisture contamination. The compound of the invention is useful to replace the halogenated hydrocarbons or as an additive. When used as an additive, there is not only an increase in lubricity and heat transfer efficiency, but also effective corrosion and moisture inhibition. Other compounds for refrigeration systems in which the composition of the invention is useful as an additive include:
  Alkyl benzene for R-22, R-11, R-502
  Polyglycols and polyol esters for use with R-134-R-32
  Mineral oil
  Polyalkylene glycols (PAG)
  For ETO or PPO (e.g., BuOH)
  PAG in automotive A/C—R-134a
  Polyalphaolefins (PAO)
  Neopentyl esters (polyol esters) reaction of alcohol and a normal branched chain carboxylic acid, e.g., pentaerythitol, trimethyl propane, neopentyl alcohol
  Complex Neopentyl esters: Reaction of polyol with a dibasic acid reaction with mixed amino acids The performance characteristics noted in experimentation include the existence of a unique extreme high pressure ingredient that has the effect of smoothing and sealing moving parts and providing protection against wear and resistance to shear so as to maintain substantive film over moving parts. Reduction of friction wear was observed to be as much as 50% with a dramatic reduction of heat. The composition also improves viscosity and acts as a corrosion fighter/acid inhibitor in addition to being a special dispersant ingredient. It helps to protect against compressor wear, reduce oil consumption, coat and protect critical engine parts, maintain A/C cleanliness and protects against thermal and viscosity breakdown.

The noted testing results on air conditioning are based on testing of a used, outdoor 4 ton package unit. The addition of 10% of the composition of the invention to the compressor oil increases the cooling efficiency of the A/C system by 10.6%. Similar improvements were obtained by adding 1.5 oz. of the composition of the invention to the compressor oil of a 18,000 BTU Kenmore™ window A/C unit. The addition of 10% of the composition of the invention to the compressor oil system reduced the energy drain on the compressor of the outdoor package unit by 4.7%.

This transesterified fatty acid ester aids in heat transfer by forming a relatively thin, non-insulating molecular layer along the inner surface of the A/C heat transfer coils. This is accomplished by the esters displacement of the relatively thick (insulating) stationary, non-laminar layer formed by the mineral oil phase along the heat transfer coil lumen.

The ester displaces the mineral oil layer by preferentially adsorbing to the A/C coil's metal surface via the electrostatic attraction between the highly polar ester moiety and the electron rich metal surface. The tenacious adhesion by the ester arises from the strong dipole and ionic forces of the phosphate and carboxylic acid ester groups. These dipoles line up so as to associate with the electron rich metal surfaces of the heat transfer coil. Once attached to the surface, the ester forms a highly adhesive/cohesive film with mid chain polar groups, such as ester and alcohol, aiding in the formation of lateral intermolecular bonding such as Van der Waals force interactions The mechanism of action of the n-propyl ester of castor oil system is based on the physical absorption of the polar ester groups via Van der Waals interaction. The n-propyl ester of castor oil, which possess a low to intermediate hydrophobic/lipophilic balance (HLB), displaces less polar groups already attached to the internal surfaces of refrigerant systems. Interestingly, highly ethoxylated esters maintain relatively high HLB as compared to the composition of the invention. The high HLB allows other esters to be readily solubilized in water while being less soluble in hydrocarbon. These traits are undesirable in refrigeration system applications since these ethoxylated esters tend to be intermediaries for the introduction of water (which promotes corrosion) and because their solubility in mineral oil systems is relatively poor. Additionally, it has not been demonstrated in the literature that the addition of ethylene oxide to an ester backbone improves overall lubricity.

Studies conducted on room air conditioners showed that the production of condensate was increased from 15-20% with the addition of the composition to a mineral oil-based system. This increase in condensate production readily translates to much improved heat transfer.

Rheological Modifier

The composition of the invention has characteristics that make the composition particularly useful for modifying rheological properties of fluid. This invention includes a process for modification of rheological properties of hydro-mechanical fluid by adding an effective amount of the transesterified fatty acid ester of the invention to the hydro-mechanical fluid.

The effective amount of the transesterified fatty acid ester is typically between about 0.5 percent to 100 percent by volume of the fluid for which the rheology is to be modified. At less than 100 percent, the composition acts as an additive. At 100 percent, the composition of the invention is the entire working fluid. More particularly, the effective amount of the transesterified fatty acid ester is from at least about 1.5 percent to about 20 percent by volume of the fluid. Preferably, the effective amount of the composition is from about 1.5 to 10 percent. For improving the lubricity of a drilling fluid, an effective amount can be less than 1.0 percent by weight of the drilling fluid. The transesterified fatty acid in both oil and water based drilling fluids greatly enhances the drilling penetration rate by significantly lowering the coefficient of friction of the drill-bit and drill solids.

The composition is useful in hydro-mechanical fluids. Hydro-mechanical fluids or working fluids are functional fluids that add utility. They are typically not process flow streams. Examples of hydro-mechanical fluids are radiator fluid, drilling fluid, engine fluid, anti-corrosive fluid, transmission fluid, hydraulic fluid, brake fluid, dielectric fluid, cutting fluid, heat transfer fluid and other fluids that perform a function of utility. The composition is particularly useful in drilling fluids to modify the theological properties of the fluids. The mechanical system can be a reciprocating combustion engine, a hydraulic braking system, a hydraulic transmission system, a coolant system or the like.

The effective amount of the cutting fluid additive is from at least about 0.1 percent to about 100 percent by volume of the composition of the invention to the cutting fluid. More particularly, the effective amount of the cutting fluid additive is from at least about 0.5 percent to about 10 percent.

The nature of the lubricant or other fluid can be widely varied by the choice of modifiers or phase transfer catalysts that can be incorporated into the hydrocarbon phase. Typical modifiers include various long chain alcohols, esters, quaternary ammonium salts, among others. The modifiers can modulate the solubility and wetting characteristics of the ester system allowing further modification of the rheological properties of the fluid to which the composition is added. Also unexpected is the fact that the nature of the absorbing ester can be varied by the choice of modifying agents, particularly in view of the requirements that the modifying agent is incorporated in the deposit in a sufficient amount to modify the latter. It was quite unexpected that the adsorption of the ester occurred so tenaciously at the surfaces.

Corrosion Inhibitor

The composition of the invention has characteristics that make the composition particularly useful as a corrosion inhibitor. The invention includes a process for inhibition of corrosion for a corrosion-susceptible mechanical system by contacting the corrosion-susceptible mechanical system with a fluid having an effective amount of the transesterified fatty acid ester of the invention in order to prevent or reduce corrosion.

The effective amount of the transesterified fatty acid ester is typically between about 0.5 percent to 100 percent by volume of the fluid for use as a corrosion inhibitor. At less than 100 percent, the composition acts as an additive to another fluid, such as a working fluid or a thin film. At 100 percent, the composition of the invention is the entire fluid. More particularly, the effective amount of the transesterified fatty acid ester is from at least about 1.5 percent to about 20 percent by volume of the fluid. Preferably, the effective amount of the composition is from about 1.5 to 10 percent. In a mechanical system with a circulating fluid, such as a heat exchanger, a preferred amount of the composition of the invention is less than about 1 percent by volume of the fluid. This amount is effective to reduce corrosion and inhibit moisture.

Examples of mechanical systems in which the composition is useful for corrosion inhibition include reciprocating combustion engines, hydraulic braking system, hydraulic transmission systems, coolant systems or the like. The invention finds utility when a thin film is created on the surface of an item to inhibit corrosion. The composition can also be used as an internal coating on pipelines to avoid corrosion. This can be achieved by adding the composition to the crude oil and gas to the pipelines or by pre-coating the pipes or by other methods known in the industry to achieve coatings on the pipe.

The composition of the invention acts as an oxidation inhibitor and prevents or controls formations of sludges and corrosive compounds as described above. It thus serves as an effective corrosion inhibitor, wherein the polar type compounds react or adsorb on metal surfaces to form passive films. The composition of the invention was found to be an effective corrosion inhibitor for iron, copper, aluminum and various alloy compositions. The corrosion rates of the metals were found to be greatly reduced over other commercially available inhibitors.

The composition can be used alone or as an additive to other inhibitors such as imidazolines, polyamines, naphthenic acid salts of fatty amines, fatty alcohols, amphoteric, quaternaries, polyesters, polyamides, polyimides ethoxylated propoxylated acids, resins and the like.

Moisture Inhibitor

The composition of the invention has characteristics that make the composition particularly useful as a moisture inhibitor. The invention includes a process for inhibition of moisture for a moisture-susceptible mechanical system by contacting the moisture-susceptible mechanical system with the fluid having an effective amount of the transesterified fatty acid ester of the invention.

The effective amount of the transesterified fatty acid ester is typically between about 0.5 percent to 100 percent by volume of the fluid for use as a moisture inhibitor. At less than 100 percent, the composition acts as an additive to another fluid, such as a working fluid or a thin film. At 100 percent, the composition of the invention is the entire fluid. More particularly, the effective amount of the transesterified fatty acid ester is from at least about 1.5 percent to about 20 percent by volume of the fluid. An example is the effective amount of the lubricant being from at least about 5 percent to about 20 percent by volume of the circulating motor oil in the reciprocating combustion engine. Preferably, the effective amount of the composition is from about 1.5 to 10 percent of the fluid. In a mechanical system with a circulating fluid, such as a heat exchanger, a preferred amount of the composition of the invention is less than about 1 percent by volume of the fluid.

Examples of mechanical systems in which the composition is useful for moisture inhibition include reciprocating combustion engines, hydraulic braking system, hydraulic transmission systems, coolant systems or the like. The composition is useful as a lubricant and/or as a corrosion inhibitor for radiators, compressors, brake and transmission fluids, hydraulic and dielectric fluids as well as additives to greases, lube and motor oils and hydrocarbon fuels.

Cleaner

The transesterified fatty acid ester of the invention is useful as a cleaner or detergent. The term detergent refers to the transesterified fatty acid ester produced from fatty acid esters that are natural or synthetic. Mechanical systems can be cleaned by adding the compound of the invention, either in pure form or as an additive, to a carrier or working fluid. An effective amount of the transesterified fatty acid ester acts to coat the mechanical systems, which can be a working or static object, to avoid deposits. It also acts as a detergent or cleaner to displace existing compounds on the surface of the mechanical system when the compounds are less polar than the composition of the invention. In this manner, the composition surplants existing materials to provide superior protection to the mechanical system. In a preferred embodiment, the fatty acid ester useful in the invention is ricinoleic acid. The compound containing a hydroxyl functional group is preferably n-propyl alcohol. The acid of a preferred embodiment is phosphoric acid.

Examples of use as a cleaner include the addition of the composition inside of a copper tubing used in a heat exchange operation that is already exposed to a polar material. The polar material on the surface of the tubing is replaced by the composition of the invention imparting the preferred characteristics of the composition to the copper tubing in the mechanical system. The other material is thus removed from the system.

EXAMPLE 1

Transesterification of Castor Oil

Commercially available castor oil generally contains about 89% ricinoleic acid with a balance of other fatty acids, lipids and organic compounds. Propyl ester and glycerol ester are naturally occurring in the mix of the fatty acid esters. For this example, commercially available castor oil is used. Pure ricinoleic acid, such as can be separated from castor oil or synthetically produced, has also been the subject of laboratory tests. The results of this novel reaction, while still excellent, vary from those using refined castor oil. Thus, the results of the embodiment using commercially available refined castor oil are discussed in this example.

This test was conducted with reactants mixed in the stoicheometric ratios as follows. Using the simplifying assumption that castor oil is 100 percent glyceryl triricinoleate, 1.0 mole of glyceryl triricinoleate is added to approximately 1.76 moles of n-propanol in the presence of about 0.026 moles phosphoric acid. The products of the reaction include propyl ricinoleate, glyceryl monoricinoleate, glyceryl diricinoleate, glyceryl triricinoleate, glycerin, n-propanol and various phosphate esters of alcohols such as phosphate esters of propyl ricinoleate, glyceryl mono, di and triricinoleate as well as phosphate esters of free glycerine and n-propanol. The term glycerol ricinoleate means mono-, di-, and tri-ricinoleate. The various phosphate esters are referred to as organophosphate esters. The ricinoleate products are generally referred to as transesterified fatty acid esters or more particularly ricinoleic n-propyl ester, an ester of ricinoleic acid, including glycerol. The transesterified fatty acid and/or the organophosphate esters include phosphated fatty acid ester when such is produced. The phosphate can be bonded or adjuvant formation. Ricinoleic acid is also known as hydroxyoleic acid The resulting reaction product mixture was measured for lubricity using the Falix test. The mixture was tested alone and in combination with other components that are used as lubricants or for heat transfer. The properties of the composition of the invention far exceed the measurements of lubricity of any known lubricant. Even in combination with other lubricants and heat transfer fluids, surprising increases in lubricity were measured. Additionally, the invention greatly enhances the efficiency of heat pump systems.

EXAMPLE 2

Transesterification of Castor Oil 2 parts USP grade castor oil is combined with 1 part of n-propyl alcohol of 99.9% purity. 0.3 to 0.35% wt/wt phosphoric acid (75%) is added to the castor oil portion of the mixture.

The components are boiled at 210F until the temperature begins to undergo a marked rise. The heating process is discontinued after a temperature of approximately 235-240° F. is reached. The mixture is then allowed to cool to room temperature. Stirring is continuous throughout the cooking process.

During the cooking process, the use of an acid catalyst accelerates a displacement reaction wherein the n-propyl alcohol replaces the glycerol associated with the carboxylic acid portion of the fatty acid (transesterification). The preferential acids are phosphoric acid and sulfuric acid; however, other acids such a muriatic and nitric acids and other organic acids as phenol sulfonic acid can serve as catalysts in the esterification process. Examples of aromatic sulfonic acids include benzene, toluene, xylenes and phenol sulfonic acids. Additionally, the phosphate or sulfate functionalities react with the hydroxyl groups present in the castor oil fatty acid structures as well as with the n-propyl alcohol and glycerine species to form their own phosphate or sulfate esters.

The preferred alcohol is n-propyl alcohol, although alcohols with carbon numbers from $C_1$ to $C_{18}$ can be used in the transesterification process. The lower chain alcohols ($C_1$-$C_4$) are the most active.

Heat transfers were conducted on copper coils, which first used a typical mineral oil composition (3GS) and compared with mineral oils containing 10% by weight of an n-propyl ester of castor oil in 3GS mineral oil. These studies were conducted at 212° F. and the n-propyl ester of castor oil found to be an excellent heat transfer agent. The temperature profile was measured at various increments along the coiled copper tubing and the n-propyl ester of castor oil was found to have a marked effect on the heat transfer (thermal conductivity) of the lubricant oil system.

The heat transfer properties of the composition of the invention make the composition particular useful for air-conditioning systems. In particular, the automotive air-conditioning sector benefits greatly from the composition not only due to the properties of the composition, but due to the non-hazardous, biodegradable nature of the composition. This eases environmental concerns regarding the maintenance and use of the composition in automotive air-conditioning systems.

The n-propyl ester of castor oil improves the heat transfer characteristics as well as greatly enhances its lubricity. Several hundred systems were evaluated by the standard pin and v-block method and the n-propyl ester of castor oil gave the best lubricating characteristics of all studied.

Based on laboratory refrigeration studies conducted on refrigeration systems ranging from small window units to a large outdoor package unit, 10% by weight of the n-propyl ester of castor oil (NPEC) added to existing mineral oil based and POE-based systems were found to improve the overall efficiency and Energy Efficiency Rating (EER) by 9-11%. The Coefficient of Performance (COP) was observed to increase from 10.54 to 11.69 with the addition of 15% by weight of NPEC. Studies conducted on room air conditioners showed that the production of condensate was increased from 15-20% with the addition of a mineral oil-based system. This increase in condensate production readily translates to much improved heat transfer.

The previous examples are illustrative and not intended to be limiting. While the examples discuss castor oil, extensive testing was conducted using a variety of fatty oil esters. Tests included contact angle, pin and V-block testing, heat coil experiments, A/C window unit evaluations, outdoor A/C package unit evaluation, solubility testing, corrosion testing, automobile A/C testing, TC/GC/MS and GC/MS Analysis, surface tension testing, TGA, DSC Analysis, SEM, EDS, ESCA and the like.

While several embodiments have been described and illustrated, it will be understood that the invention is not limited thereto since many modifications can be made and equivalent structures will become apparent to those skilled in the art to which the invention pertains. For example, the term fluid is used throughout to include those fluids specifically identified, such as lubricants, heat transfer fluid, rheological fluid, anti-corrosion fluids and moisture inhibition fluids, as well as other fluids that perform a function or benefit from the addition or substitution of the composition of the invention with its specific properties. For example, the composition of the current invention can be used as the fluid or as an additive to the fluid to lubricate the bore of guns. This increases velocity of a bullet, reduces heat to the bore and reduces rust.

We claim:

1. A composition comprising reaction products from a reaction of a ricinoleic acid with propyl alcohol in the presence of a phosphorus-containing acid, the reaction products including a propyl ester of ricinoleic acid formed through partial transesterification, and a phosphorus-containing compound, the reaction products exhibiting solubility with refrigerant, hydrocarbons or fuel solvents.

2. The composition of claim 1 wherein castor oil is used in the reaction to supply the ricinoleic acid.

3. The composition of claim 1 wherein the transesterified fatty acid ester includes ricinoleic n-propyl ester.

4. The composition of claim 1 wherein the reaction produces a phosphated fatty acid ester.

5. The composition of claim 1 wherein the reaction produces glycerol ricinoleate and n-propyl ricinoleate.

6. The composition of claim 1 wherein the fatty acid ester is dimerized or trimerized.

7. The composition of claim 1 wherein the acid is phosphoric acid.

8. The composition of claim 1 wherein the propyl ester of ricinoleic acid contains a phosphate functional group.

9. The composition of claim 1 wherein the propyl alcohol comprises isopropyl alcohol.

10. The composition of claim 1 further comprising reaction with a second alcohol wherein the second alcohol is butyl alcohol.

11. The composition of claim 1 wherein the propyl alcohol comprises n-propyl alcohol.

12. The composition of claim 1 further comprising a miscibility-enhancement additive effective to increase miscibility with naphthenes, paraffins, alkyl benzenes, mineral oils, polyol esters, polyalphaolefins, polyalkylene glycols, polybutenes, polyvinyl ethers and substituted hydrocarbons.

13. A process for lubrication of a lubricant-dependant system with a fluid, the process comprising the step of adding an effective amount of the composition of claim 1 to the fluid in the lubricant-dependant system.

14. A process for increasing heat transfer in a heat transfer system capable of receiving a heat transfer fluid, the process comprising the step of adding an effective amount of the composition of claim 1 to the heat transfer fluid.

15. A process for modification of rheological properties of a hydro-mechanical fluid, the process comprising the step of adding an effective amount of the composition of claim 1 to the hydro-mechanical fluid.

16. A process for inhibition of corrosion for a corrosion-susceptible mechanical system, the process comprising the step of contacting the corrosion-susceptible mechanical system with a fluid having an effective amount of the composition of claim 1.

17. A process for inhibition of moisture for a moisture-susceptible mechanical system, the process comprising the step of contacting the moisture-susceptible mechanical system with a fluid having an effective amount of the composition of claim 1.

18. The process of claim 13, wherein the composition further comprises a miscibility-enhancement additive effective to increase miscibility with napthenes, paraffins, alkyl benzenes, mineral oils, polyol esters, polyalphaolefins, polyalkylene glycols, polybutenes, polyvinyl ethers and substituted hydrocarbons.

19. The process of claim 13 further comprising the step of reacting the transesterified fatty acid ester with a second compound having an acetyl, alkyl oxy, alkyl propoxy or carboxyl functional group to form a further-substituted fatty acid ester that includes an acetyl, alkyl oxy, alkyl propoxy or ester functional group.

20. The process of claim 13 wherein the lubricant-dependant system is selected from the group consisting of a mechanical device, a refrigeration system, a motor oil system, an engine, an engine part, a gear, a drilling operation and a reciprocating combustion engine.

21. The process of claim 13 wherein the composition is capable of providing lubrication at temperatures up to about 350 degrees C.

22. The process of claim 13 wherein the composition lubricant is capable of providing lubrication below 0 degrees C.

23. The process of claim 14 wherein the heat transfer system is selected from the group consisting of a coolant system, a hydraulic braking system, a hydraulic transmission system, a refrigeration system and an air-conditioning system.

24. The process of claim 15 wherein the hydro-mechanical fluids is a functional fluids.

25. The process of claim 15 wherein the hydro-mechanical fluid is selected from the group consisting of radiator fluid, drilling fluid, engine fluid, anti-corrosive fluid, transmission fluid, hydraulic fluid, brake fluid, dielectric fluid, heat transfer fluid and cutting fluid.

26. The process of claim 16 wherein the mechanical system is a reciprocating combustion engine, a hydraulic braking system, a hydraulic transmission system or a coolant system.

27. The composition of claim 1 wherein: the composition is effective in providing lubrication to a mechanical system; the transesterified fatty acid ester has an HLB between about 0.5 and 4.8; and the transesterified fatty ester exhibits in excess of 1000 pounds force load to failure.

28. A process for cleaning a mechanical system, the process comprising the step of contacting the mechanical system with a fluid having an effective amount of the composition of claim 1.

29. The process of claim 28, wherein the propyl alcohol is n-propyl alcohol.

30. The process of claim 28, wherein the phosphorus-containing acid is phosphoric acid.

31. A method of making a phosphorus-containing composition comprising the steps of:
reacting a fatty acid ester comprising ricinoleic acid with propyl alcohol in the presence of a phosphorus-containing acid such that the reaction products include a propyl ester of ricinoleic acid formed through partial transesterification and a phosphorus-containing compound, the phosphorus-containing composition exhibiting solubility with refrigerant, hydrocarbons or fuel solvents.

* * * * *

UNITED STATES PATENT AND TRADEMARK OFFICE
CERTIFICATE OF CORRECTION

| | |
|---|---|
| PATENT NO. | : 7,968,504 B2 |
| APPLICATION NO. | : 11/821689 |
| DATED | : June 28, 2011 |
| INVENTOR(S) | : Benjamin Mosier and Bryan J. Duffy |

It is certified that error appears in the above-identified patent and that said Letters Patent is hereby corrected as shown below:

In the claims:

On column 18, line 34:
    the first word in the sentence "fluids" please change to "fluid"
    the fifth word in the sentence "fluids" please change to "fluid"

Signed and Sealed this
Ninth Day of August, 2011

David J. Kappos
*Director of the United States Patent and Trademark Office*